(12) United States Patent
Merchant (10) Patent No.: US 11,491,275 B2
(45) Date of Patent: Nov. 8, 2022

(54) CLOSED SYSTEM ELASTOMERIC PUMPING MECHANISM

(71) Applicant: Michael A. Merchant, Franklin, MA (US)

(72) Inventor: Michael A. Merchant, Franklin, MA (US)

( * ) Notice: Subject to any disclaimer, the term of this patent is extended or adjusted under 35 U.S.C. 154(b) by 132 days.

(21) Appl. No.: 16/244,576

(22) Filed: Jan. 10, 2019

(65) Prior Publication Data

US 2019/0209775 A1 Jul. 11, 2019

Related U.S. Application Data

(60) Provisional application No. 62/616,037, filed on Jan. 11, 2018.

(51) Int. Cl.

| | |
|---|---|
| *A61M 5/168* | (2006.01) |
| *A61M 39/08* | (2006.01) |
| *A61M 5/155* | (2006.01) |
| *A61M 5/142* | (2006.01) |
| *A61M 5/14* | (2006.01) |

(Continued)

(52) U.S. Cl.
CPC ...... *A61M 5/16881* (2013.01); *A61M 5/1413* (2013.01); *A61M 5/14212* (2013.01); *A61M 5/155* (2013.01); *A61M 5/16831* (2013.01); *A61M 39/08* (2013.01); *A61M 39/26* (2013.01); *A61M 2039/2486* (2013.01)

(58) Field of Classification Search
CPC .... A61M 2039/268; A61M 2039/2406; A61M 2039/262; A61M 2039/2426; A61M 2039/2433; A61M 2039/244; A61M 2039/1027; A61M 2039/2486; A61M 2039/246; A61M 39/26; A61M 39/24; A61M 39/12; A61M 5/16881; A61M 5/16804; A61M 5/1413; A61M 5/155; A61M 5/16831; A61M 5/14212; A61M 5/14216; A61M 5/14244; A61M 5/14228; F16K 31/00; F16K 31/44; F16K 31/147; F16K 31/181; F16K 31/188
See application file for complete search history.

(56) References Cited

U.S. PATENT DOCUMENTS

| | | | | |
|---|---|---|---|---|
| 4,813,937 A | * | 3/1989 | Vaillancourt | ......... A61M 5/145 |
| | | | | 128/DIG. 12 |
| 5,492,147 A | * | 2/1996 | Challender | ........... F16L 29/005 |
| | | | | 137/614.05 |

(Continued)

*Primary Examiner* — James D Ponton
(74) *Attorney, Agent, or Firm* — Armis IP Law, LLC (57) ABSTRACT

A medicinal infusion system includes a safety valve for isolating residual medication by providing a single point of fluidic disconnect to encapsulate a residual fluid volume prone to spillage. The safety valve couples a medicinal repository such as an infusion pump to a medicinal supply, typically from a syringe or tubing. The safety valve includes a resilient, deformable, or hinged surface for isolating and sealing the medicinal flow to eliminate and/or isolate any residual volume in tubing and connectors. The isolating surface accommodates an inserted fitting or coupling for allowing the medicinal flow to fill the infusion pump. Upon disconnection, fluids on either side of the safety valve are therefore isolated on the respective fill or source sides, and residual volume prone to spillage is eliminated.

12 Claims, 8 Drawing Sheets

(51) Int. Cl.
*A61M 39/26* (2006.01)
*A61M 39/24* (2006.01)

(56) References Cited

U.S. PATENT DOCUMENTS

| | | | | |
|---|---|---|---|---|
| 5,578,059 | A * | 11/1996 | Patzer | A61M 39/045 |
| | | | | 251/149.1 |
| 5,727,594 | A * | 3/1998 | Choksi | A61M 39/24 |
| | | | | 137/537 |
| 2004/0102738 | A1* | 5/2004 | Dikeman | A61M 39/24 |
| | | | | 604/256 |
| 2005/0087715 | A1* | 4/2005 | Doyle | F16K 15/185 |
| | | | | 251/149.1 |
| 2013/0030387 | A1* | 1/2013 | Williams | A61M 39/26 |
| | | | | 604/256 |
| 2013/0204226 | A1* | 8/2013 | Keyser | A61M 25/0097 |
| | | | | 604/506 |
| 2014/0228778 | A1* | 8/2014 | Ma | A61M 39/221 |
| | | | | 604/256 |

\* cited by examiner

CLOSED SYSTEM ELASTOMERIC PUMPING MECHANISM

RELATED APPLICATIONS

This application claims the benefit under 35 U.S.C. § 119(e) of U.S. Provisional Patent Application No. 62/616,037, filed Jan. 11, 2018, entitled "CLOSED SYSTEM ELASTOMERIC PUMPING MECHANISM" incorporated herein by reference in entirety

BACKGROUND

Medical, scientific and research environments often rely on flexible tubing for conveying fluids. IV (intravenous) fluids are often administered in medical contexts through flexible tubing to a needle or central line inserted into a bloodstream of a patient. LUER-LOK® (luer) connectors are commonly used for interconnection of lines (tubing) used for IV and medicinal purposes, such as infusion delivery via an infusion pump. Luer connections provide a fast and efficient coupling of fluid lines and vessels through threaded or frictionally engaged, standard sized fittings and adapters that mate with corresponding male or female counterparts. Once proprietary, luer connectors have substantially merged with common medical terms and devices.

SUMMARY

Mated connections such as luer-based tubing junctions allow efficient, interconnections for medicinal transport for IV applications. Male and female luers typically permit fluid flow only when engaged with a corresponding male or female counterpart. This valving effect prevents potentially hazardous spillage of residual medicine in the tubing used for transport. Fluid flow of the transported IV medication is driven by low pressure sources such as elastomeric infusion pumps, electromechanical infusion pumps, and simple elevated IV bags. However, conventional infusion pumps do not incorporate valves or fluid retention capabilities for ensuring that contained medication cannot drip or spill from the pump upon connection/disconnection of fill and supply lines. It would be beneficial to provide an infusion pump integrated with valving and fluid encapsulation properties for preventing inadvertent release of potentially hazardous medication during interconnection with tubing and vessels required for use.

Configurations herein provide a medicinal infusion system including a safety valve for isolating residual medication by providing a single point of fluidic disconnect and unidirectional flow to encapsulate a residual fluid volume prone to spillage. The safety valve couples a medicinal repository such as an infusion pump to a medicinal supply, typically from a syringe or tubing. The safety valve includes a resilient, deformable, or hinged surface for isolating and sealing the medicinal flow to eliminate and/or isolate any residual volume in tubing and connectors. The isolating surface accommodates an inserted fitting or coupling for allowing the medicinal flow to fill the infusion pump. Following the fill, disconnection of the fill fitting causes the isolating surface to close and seal the medicinal volume in the pump. Concurrently, the ingress fitting has an inner or concentric protrusion responsive to disengagement with the safety valve for isolating any residual fluid volume in the fill tubing or syringe. Fluids on either side of the safety valve are therefore isolated on the respective fill or source sides, and residual volume prone to spillage is eliminated.

In contrast to conventional approaches, following patient use, the fill syringe and associated tubing may be safely disposed with the encapsulated fluid, or alternatively may be recovered by controlled approaches. Residual medication that would have otherwise remained in tubing and connectors, prone to spillage, drips and leakage, is sealed and encapsulated. Configurations herein are based, in part, on the observation that residual medication contained in connection and delivery apparatus can be detrimental to handling personal due to surface irritations, transdermal absorption, and subsequent collateral contact. Medicinal waste also increases expense in the case of high cost medications. Unfortunately, conventional approaches suffer from the shortcoming that packaging and delivery devices, such as LUER-LOK® (luer) connectors, are not employed or disposed to embrace the entire medicinal path. Residual volumes remain in tubing lengths and adaptors which can spill or drip when handled or disposed. For example, a tubing length may have a luer connector followed by a tubing length that retains residual medication, or an adapter contains a volume following disconnection from a fitting or luer connector. Or the needed luer connectors may not be available. Accordingly, configurations herein substantially overcome the shortcomings of residual volumes by providing a safety valve that defines a single point of fluidic disconnect for filling or dispensing a medicinal quantity. The safety valve has isolating surfaces or elastomeric structures that resiliently or deformably seal around an inserted or withdrawn fitting for isolating the fluid volume prior to any drippage or spillage, effectively encapsulating any escaping residual volume.

In one configuration, a safety valve may be implemented by employing a system of luer connectors including opposed, sealable vessel openings on each side of mating connectors so as to prevent accidental spillage or loss of contained liquid upon decoupling. Infusion line or tubing used for providing intravenous (IV) medication is typically coupled using a luer connector. The IV medication may be hazardous to handlers of the IV, such as lab, pharmacy and nursing personnel through surface irritation and transdermal absorption. The luer connectors include an engaging portion and a sealing portion. The engaging portion engages a receptacle portion on an opposed luer connector, and are typically referred to as "male" and "female" connectors. A sealing portion includes a compressible resilient material designed to provide a sealing engagement between engaged luer connectors.

However, the luer system employs a plurality of fittings and connectors in a particular sequence. The number and arrangement of parts can introduce complexity and cost. It would be beneficial to provide a safety valve configuration integrated in a medicinal pumping device such as an elastomeric infusion pump, including a medicinal repository adapted to store a volume of fluid for intravenous injection. The infusion pump includes an ingress port configured to receive the volume of fluid, and a safety valve connected between the ingress port and the medicinal repository, such that the safety valve is operable to engage an ingress fitting for permitting unidirectional fluidic transfer from the ingress fitting into the medicinal repository when engaged. A closure in the safety valve is adapted to seal the ingress port upon disengagement of the ingress fitting for retaining fluid in either the medicinal repository or a vessel supplying the ingress fitting, therefore leaving residual medication safely encapsulated in the tubing and connectors.

BRIEF DESCRIPTION OF THE DRAWINGS

The foregoing and other objects, features and advantages of the invention will be apparent from the following description of particular embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION

The following detailed description sets forth numerous specific details to provide a thorough understanding of the invention. However, those skilled in the art will appreciate that the invention may be practiced without these specific details. In other instances, well-known methods, procedures, components, protocols, processes, and circuits have not been describe in detail so as not to obscure the invention as claimed.

Where a term is provided in the singular, the inventors also contemplate aspects of the invention described by the plural of that term. As used in this specification and in any claims, the singular forms "a", "an", and "the" include plural references unless the context clearly dictates otherwise, e.g. "a derivative work". Thus, for example, a reference to "a method" includes one or more methods, and/or steps of the type described therein and/or which will become apparent to those persons skilled in the art upon reading this disclosure.

The terms "include", "includes", "including", "comprising" and variations thereof mean "including but not limited to", unless expressly specified otherwise. The term "consisting of" and variations thereof includes "including and limited to", unless expressly specified otherwise.

The phrase "based on" does not mean "based only on", unless expressly specified otherwise. In other words, the phrase "based on" describes both "based only on" and "based at least on". The term "represent" and like terms are not exclusive, unless expressly specified otherwise.

Configurations disclosed below depict safety valve configurations for providing a single disconnection point that isolates a medicinal quantity following transport through an arrangement of tubes and fittings for patient administration. Elimination of intermediate fittings and adaptors avoids an open tubing length that can drip or spill a residual quantity of medicinal liquid remaining in the tubes and connectors. In one configuration, the disclosed system employs fittings and connectors employing LUER-LOK® based parameters, as defined in ISO 80369-7:2016, which specifies dimensions and requirements for the design and functional performance of small-bore connectors intended to be used for connections in intravascular applications or hypodermic connections in hypodermic medical devices and accessories. In another configuration, a safety valve integrated with an infusion pump apparatus provides a single point of fluidic disconnect and unidirectional flow to mitigate any residual fluid volume prone to spillage.

Figure 1:
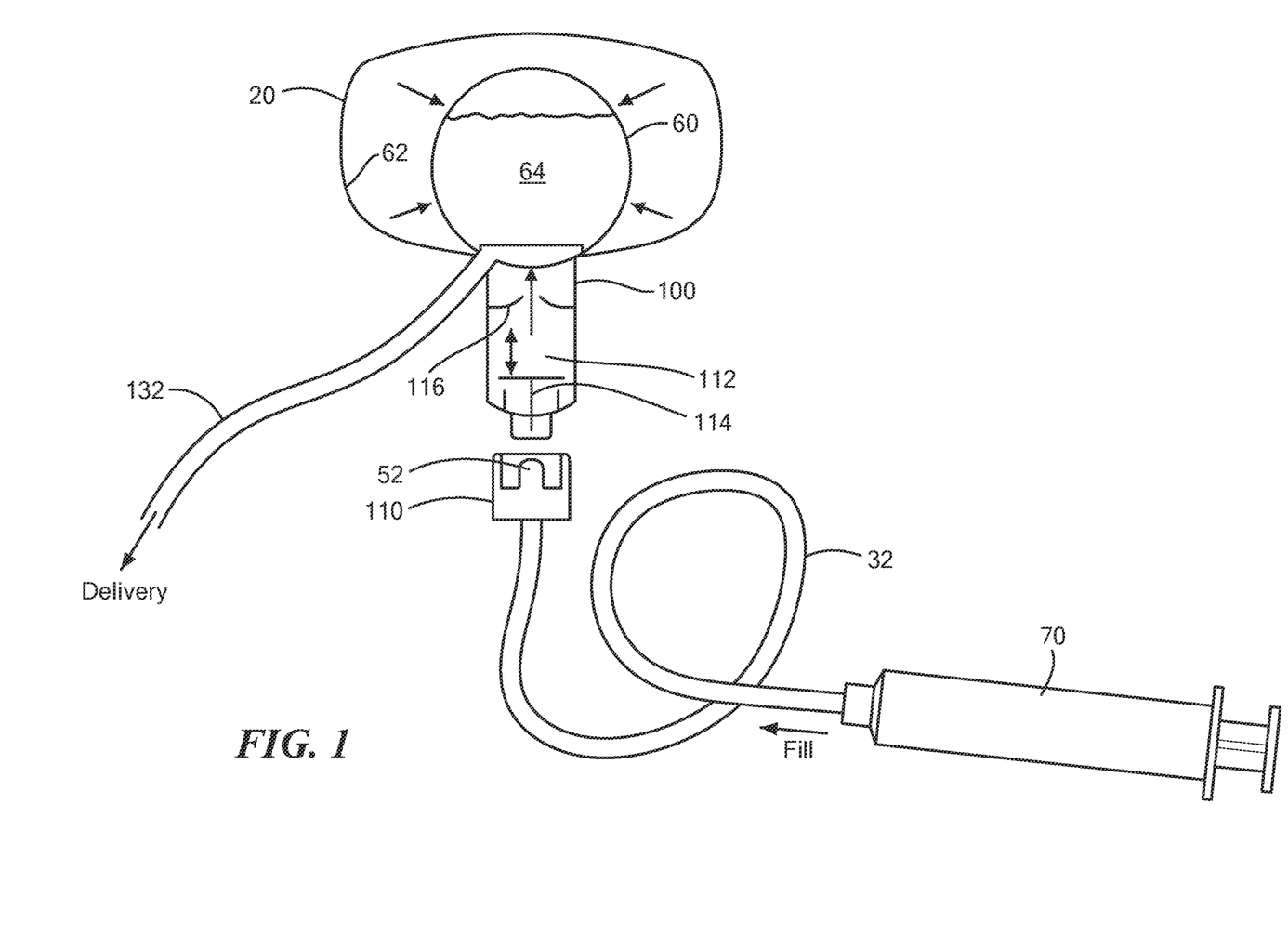
FIG. 1 shows a safety valve integrated in a medicinal fluidic pumping and delivery apparatus.

FIG. 1 shows a schematic diagram of fluid flow and valving in a safety valve 100. The safety valve 100 operates in conjunction with a fluidic vessel 20 employed for infusion based medication delivery. The fluidic vessel 20 may be an elastomeric infusion pump or other apparatus for controlled dispensing of IV medication. The fluidic vessel 20 includes an elastic storage containment 60, or medicinal repository, surrounded by an expandable surround 62 which is responsive to air pressure for forcing the storage containment to contract. Fluidic medication 64 is forced out the delivery vessel 132 for IV based transport to a patient.

The fluidic medication 64 fills the containment 60 from a fill tube 32, usually administered by a pharmaceutical or hospital technician through a syringe 70 or other dispensing apparatus. As indicated above, spillage and residual medication exposure present a hazard from the risk of contact.

The safety valve 100 includes a series of valves and checks to ensure that a residual volume 112 of medication cannot be liberated flow or spill onto surrounding surfaces or personnel. A pressure activated valve 114 resiliently travels between sealed and open positions based on a protrusion 52 at a fill tube 32 closed male luer 110. The valve 114 ensures that fluidic passage is allowed only when the fill tube 32 is connected, and upon disconnection, closes such that the residual volume 112 is retained. The safety valve 100 also employs a unidirectional valve 116 controlling ingress to the medication containment 60. In the example arrangement, the pressure activated valve 114 and unidirectional valve 116 may be implemented by resilient, elastomeric structures. In another configuration discussed below, they are defined by a single disconnection point.

A delivery tube or vessel 132 connects to a delivery port or egress from the containment for administration to a patient. The delivery port couples to the delivery vessel 132, and has a closed male luer at the patient connection adapted to retain residual fluid upon disconnection from patient delivery, thereby encapsulating liquid contained in the delivery vessel 132 from spillage.

The unidirectional valve ensures that dispensed medication passes only through the delivery vessel 132, and further guards against inadvertent dispensing of the medication 64. In contrast to conventional approaches, the safety valve 100 provides functional fill capability for infusion via the vessel 20, while guarding against stray residual medication prone to spillage or contamination of surrounding persons or equipment.

Figure 2:
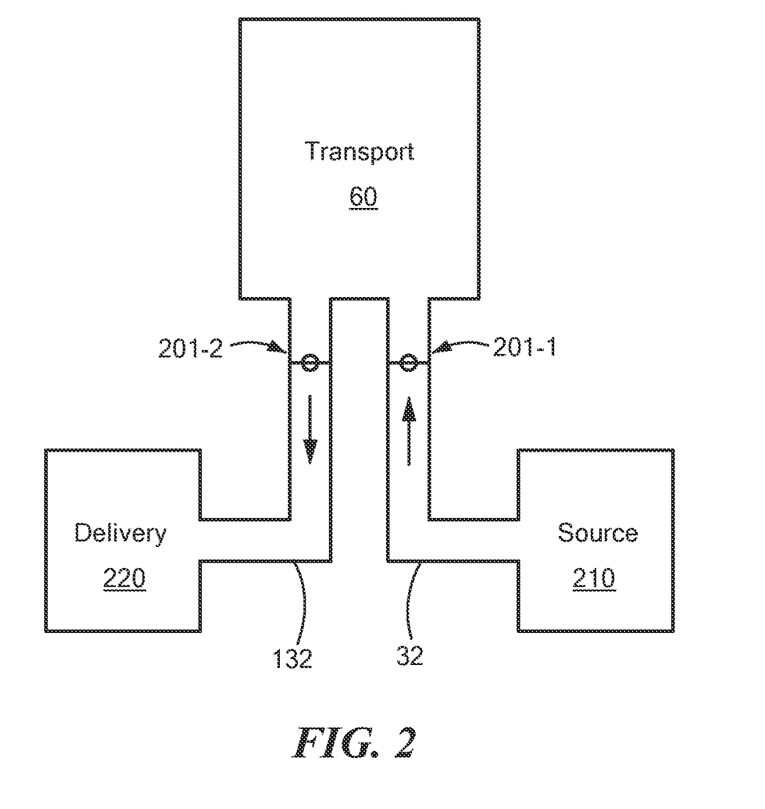
FIG. 2 is a schematic diagram of fluid flow and valving in the safety valve of FIG. 1.

FIG. 2 is a schematic diagram of fluid flow and valving principles exhibited by the safety valve 100 of FIG. 1. Referring to FIGS. 1 and 2, a feature of the disclosed approach is to employ an isolating disconnect point that blocks residual fluid from flowing or leaking back out from tubing or fittings carrying the medication. Medication delivery emanates from a source 210, fills an infusion pump or other transport containment 60, and passes to a patient for delivery 220. The source 210 of medication, typically flowing from a syringe or similar pressure source, fills the containment 60 within the fluidic vessel 20 in preparation for patient infusion. The safety valve 100 provides a single point of fluidic disconnect 201-1 and unidirectional flow to encapsulate the fluid volume prone to spillage. Upon disconnection, following a fill operation, all medication 64 is retained either in the containment 60 or sealed in the fill tube 32. Similarly, on the delivery vessel 132, a single point of disconnection 201-2 (201 generally) seals all transitional medication either in the containment 60 or the delivery vessel 132. The delivery side fluidic disconnect 201 may be disposed adjacent the patient or the containment; in either case residual fluidic volume in the upstream delivery vessel 132 remains sealed. The disconnection points 201 define a fluidic junction point for encapsulating residual vessel volume at a unidirectional decoupling based on a medication flow direction.

Figure 3:
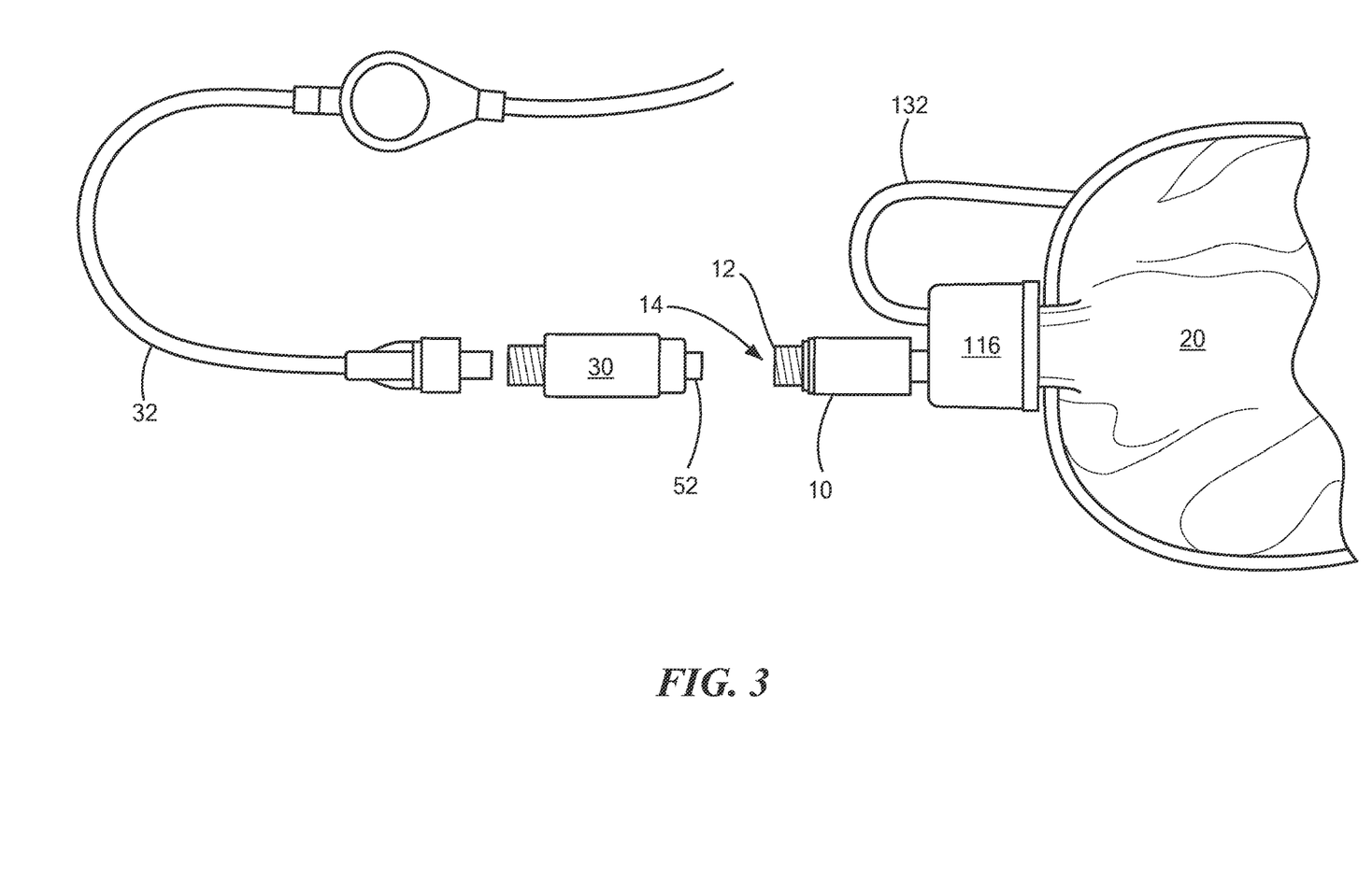
FIG. 3 shows a luer system depicting a medical infusion line coupler device in an uncoupled state.
Figure 4:
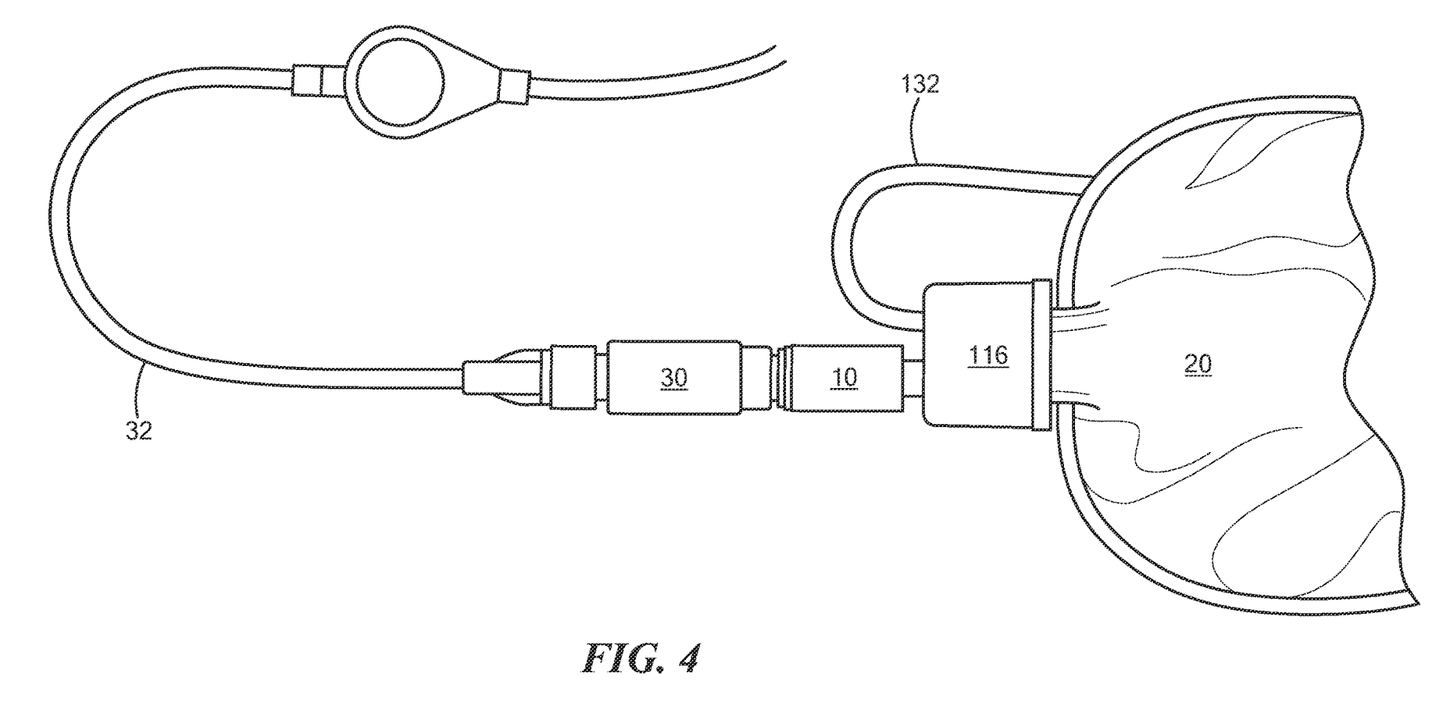
FIG. 4 shows a coupled, or engaged state of the system of FIG. 3.

FIG. 3 shows a safety luer lock configuration depicted as a medical infusion line coupler device in an uncoupled state, and FIG. 4 shows a coupled, or engaged state. The examples of FIGS. 3 and 4 show separate interconnections for the unidirectional 116 and pressure activated 114 valves. Other alternative approaches may also be envisioned for implementing the safety valve 100 in conjunction with an infusion pump, such as the infusion pump and integrated safety valve disclosed below in FIGS. 5A-5D, or other arrangement of valves and fluid vessels for ensuring retention of the residual volume 112. The device includes a standardized fluidic coupling having an engageable one-way valve on an ingress fitting 10 from a fluid vessel 20. The valve is a resilient check valve 12, and imposes an interference path 14 against fluid contained in the ingress fitting 10. The ingress fitting 10 mates with a closed male luer 30 in communication with a fill tube 32 and/or syringe 70 for filling the fluid vessel 20 in anticipation of intravenous fluidic transport to a patient. An engageable linkage between the resilient check valve 12 and the closed male luer 30 is configured to retain residual fluid during disengagement.

In the example configuration of FIGS. 3 and 4, the safety valve 100 is defined by a resilient, sealable element disposed in an interference manner with a fluid path through the ingress fitting 10, typically an elastomeric, rubber or polymer adapted to deform upon insertion of the mating closed male luer 30. The closed male luer 30 has a protrusion 52, such that the one-way valve is responsive to the protrusion for permitting fluid flow from the fill tube 32 through the ingress fitting 10. Upon engagement for filling the vessel 20, shown in FIG. 4, the protrusion 52 is disposed for deformation of the resilient, sealable element upon engagement of the engageable linkage, such that the deformation disengages interference 14 with the fluid path. Upon disengagement, the protrusion 52 closes and allows the resilient sealable element to revert back to an undeformed state to form an interference engagement 14 (path) preventing liquid from exiting the ingress fitting 10.

The protrusion 52 is likewise adapted to retain residual fluid within the closed male luer 30 during disengagement of the engageable linkage. In the example arrangement, the engageable linkage provides a threaded engagement between the ingress fitting 10 and the closed male luer 30 for tight sealing during medicinal fill operations.

FIGS. 5A-5D show a cutaway view of a safety valve as in FIG. 1 or 2. In FIG. 5A-5D, an alternate configuration of the safety valve 200 is shown for depicting the manner of fluid retention. Rather than an arrangement of luer connectors and check valves in series, the single disconnection points 201 are defined by an integrated safety valve 200 adapted for integration with an infusion pump as in FIG. 1. The integrated safety valve 200 and infusion pump are deployable as a single unit to mitigate multiple parts that increase complexity and the possibility of connection errors.

Referring to FIGS. 5A-5D, the safety valve 200 includes a closure 230 responsive to engagement with an ingress fitting 240. The closure 230 in the safety valve 200 is adapted to seal an ingress port 232 upon disengagement of an ingress fitting 240 for retaining fluid in either the medicinal repository or the fill tube 32 (vessel) supplying the ingress fitting 240. The safety valve 200 may be responsive to a luer connector or other ingress fitting.

In the example of FIGS. 5A-5D, the closure 230 is responsive to a protrusion 242 on the ingress fitting for permitting fluid flow, in which the protrusion 242 is responsive to engagement with the ingress port 232 for permitting fluid flow only when engaged. The closure includes one or more interference surfaces 250-1 . . . 250-2 (250 generally) configured to dispose into a sealing engagement with the ingress port 232, shown in FIG. 5A. From an initially closed position in FIG. 5A, the interference surface 250 is adapted to dispose in response to the protrusion 242 on the ingress fitting 240 at the end of the fill vessel 32.

Upon insertion, the protrusion 242 disposes the interference surface 250 as shown in FIG. 2B. The interference surface 250 may be is hingedly attached to an outer wall of the ingress port 232 for opening inward towards an interior of the medicinal repository 60 in response to the inserted protrusion on the ingress fitting or pressure from a fluidic inflow into the medicinal repository, such that the interference surface returns to a closed position upon either reverse fluid flow or protrusion retraction. The closure 230 may include a resilient surface adapted to deform towards an inflow direction into the medicinal repository 60 in response to the protrusion on the ingress fitting, and adapted to revert to a closed position from at least one of retraction from the protrusion or outflow pressure from the medicinal repository. The protrusion 242 displaces the interference surfaces 250 towards the walls of the ingress port 232 as it is inserted, shown in FIG. 5B.

Figure 5A:
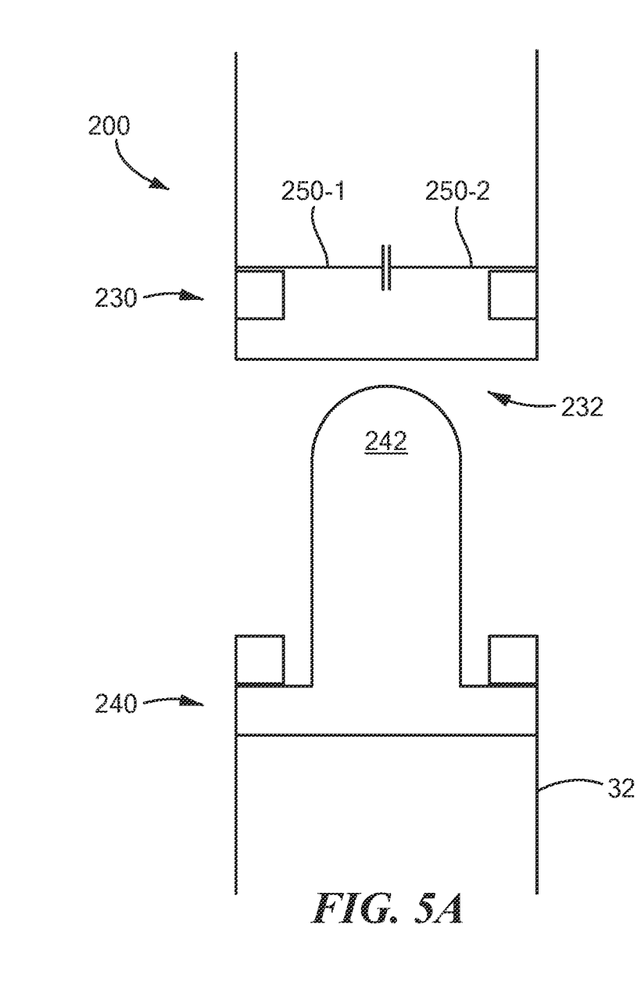
FIGS. 5A-5D show a cutaway view of an alternate configuration of a safety valve as in FIG. 1.
Figure 5B:
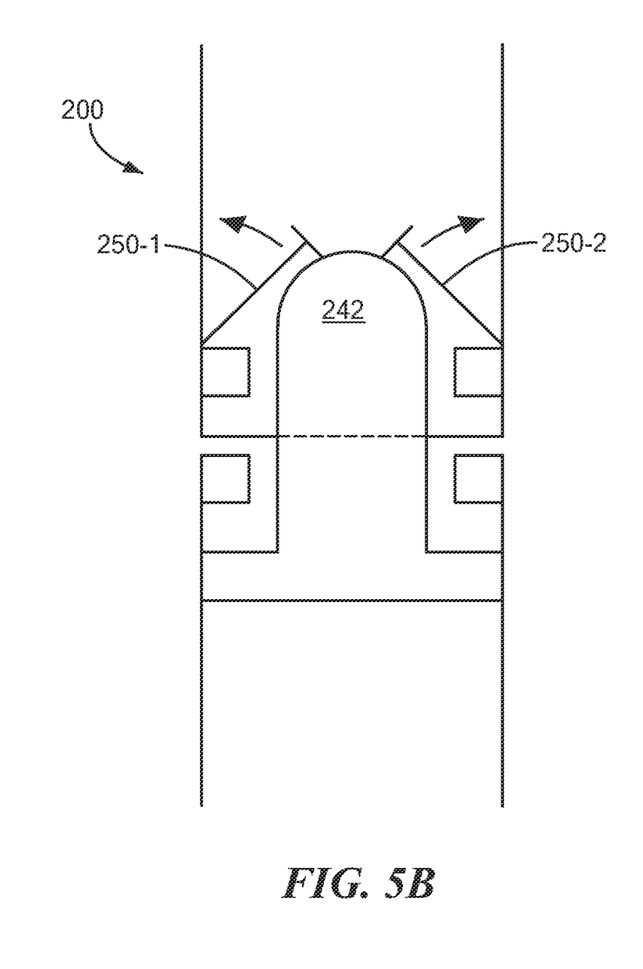
Figure 5C:
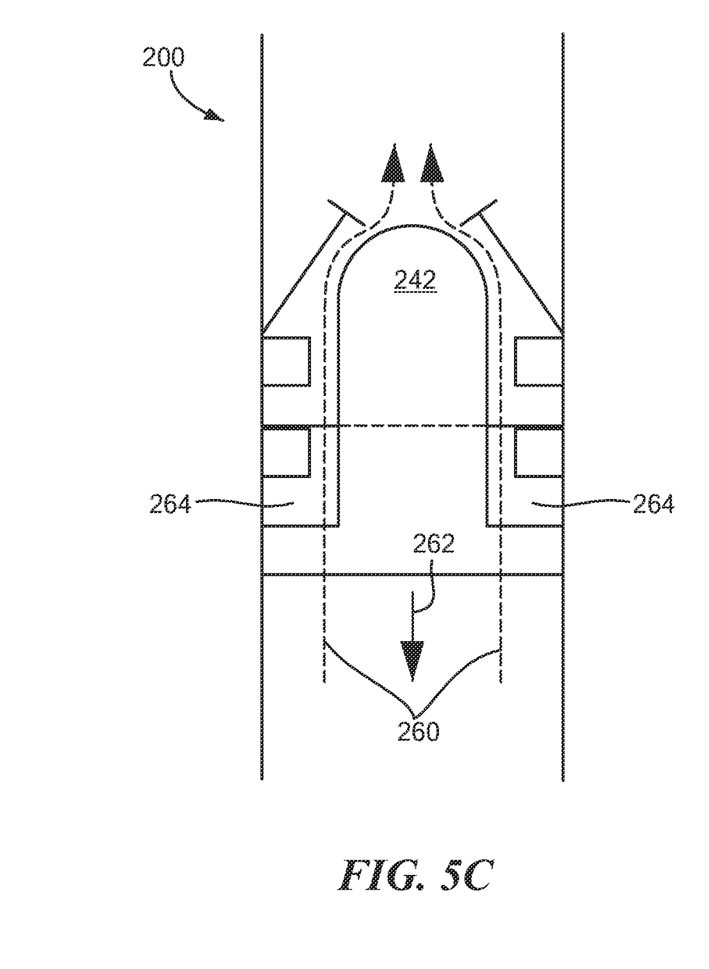
Figure 5D:
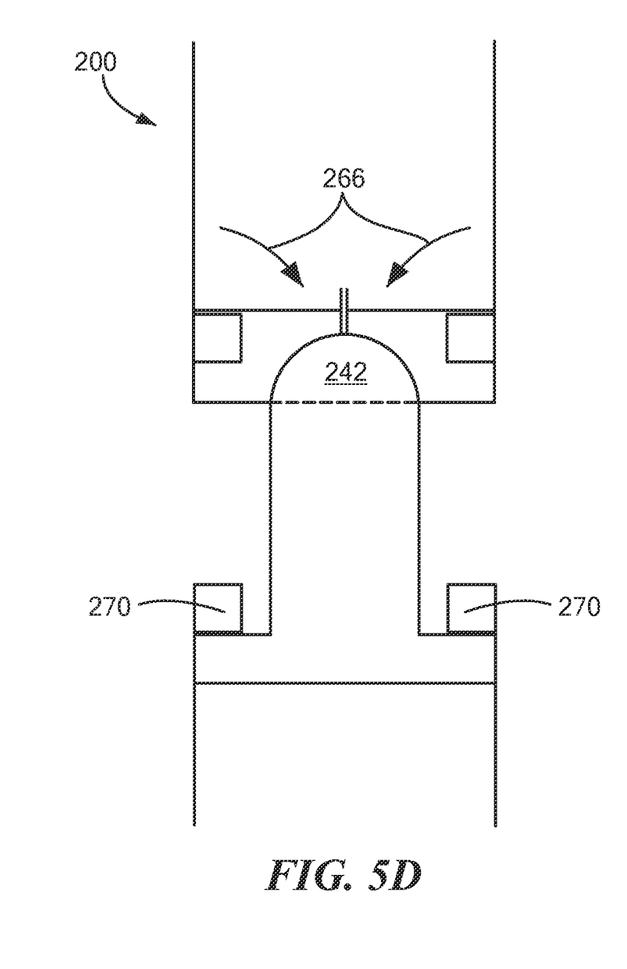

In FIG. 5C, the interference surface 250 is responsive to permit fluid ingress based on fluidic flow into the medicinal repository and restrict outflow through the ingress port in response to reverse fluidic pressure, thus enforcing unidirectional flow. Dotted arrows 260 depict the direction of fluid flow. Simultaneously, the interference surfaces 250 force the protrusion backwards toward the fluid source, shown by arrow 262. The protrusion 242 is therefore responsive to engagement with the ingress port for permitting fluid flow only when engaged, as the backwards movement of the protrusion 242 opens fluid channels 264 for permitting flow from the fill vessel 32.

Following a fill of the repository 60, the interference surface 250 is adapted to dispose to a sealed position responsive to fluidic pressure in an outflow direction from the medicinal repository, shown by arrows 266. The safety valve 200 is adapted to retain residual fluid volume upon disconnection from a transfer or supply vessel 32 as the interference surface 250 resiliently disposes to a closed position in FIG. 5D from either reverse fluid pressure or protrusion 242 removal. As the protrusion 242 is removed, it displaces back against a stop ring 270 to close fluid passages 264 and seal the fill vessel 232. Interference surfaces 250 simultaneously seal the ingress port 232.

Figure 6:
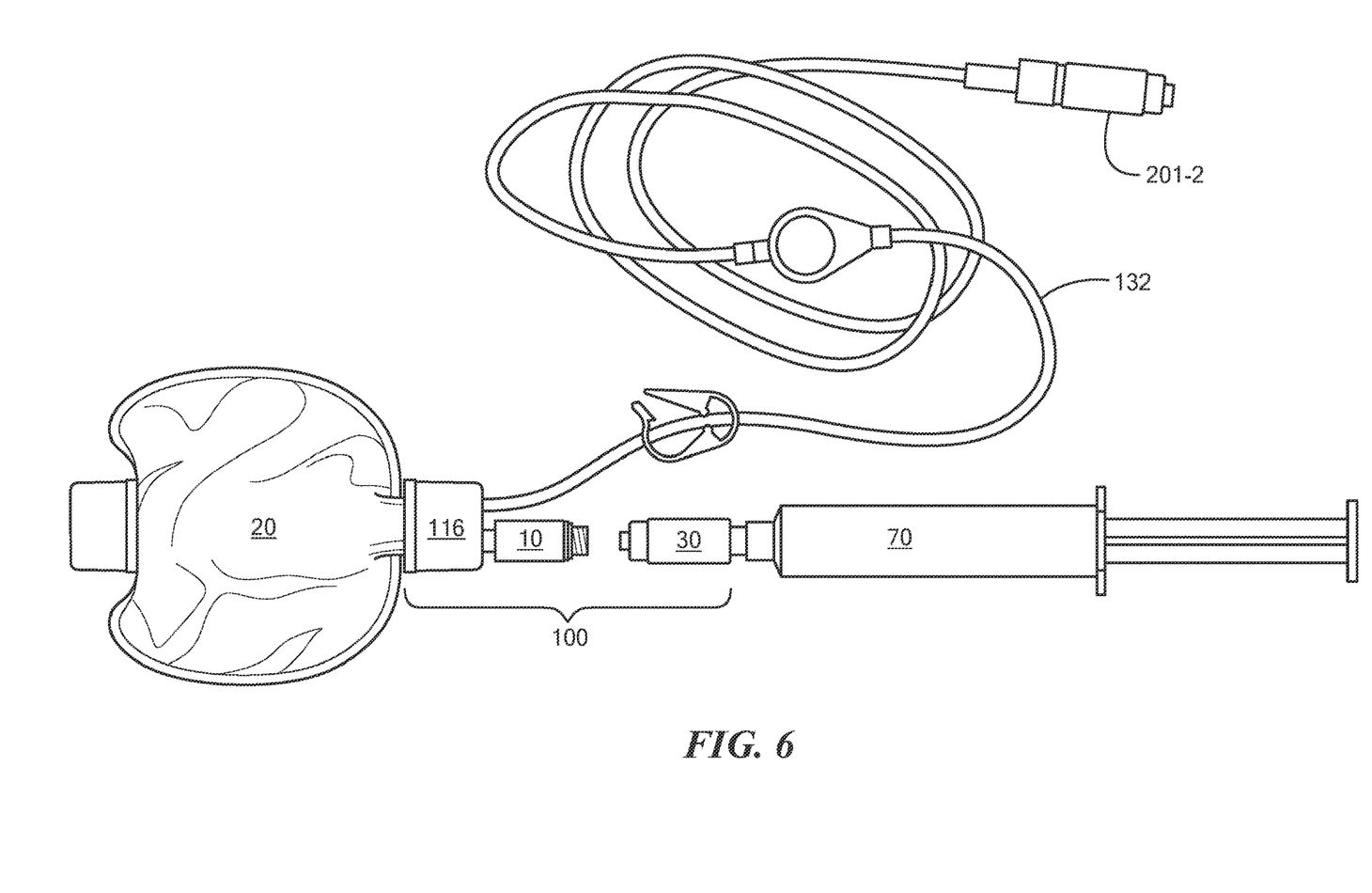
FIG. 6 shows a direct connect system implementing a safety valve fluidic linkage.

FIG. 6 shows a direct connect system implementing a safety valve fluidic linkage. Conventional approaches to IV medication employ a prescribed quantity of medication delivered to the medicinal repository in the infusion pump, defined by supply vessel 20. The prescribed quantity is often measured via a syringe 70 for ease of measurement and ability to generate a pressurized flow into the repository. In addition to the safety valve 100, configurations herein include a delivery system comprising the ingress fitting 10 having the protrusion, and a check valve, optionally with a unidirectional coupling, attached at the end of the delivery vessel 132 for patient injection. The delivery vessel 132 engages a preexisting medication conduit, such as a central line, IV line or other fluidic connection to a patient bloodstream for receiving the medication. The delivery side disconnection point 201-2 is defined by a closed male luer connection that seals upon disconnection to isolate the supply vessel 132. The complete system including the infusion pump with integrated safety valve, ingress fitting 10 and syringe 70, and delivery vessel and check valve, defines a complete system for isolating all residual medicinal fluid and encapsulating the fluid in the pump system, preventing contact with medical personnel. The safety valve 100 may be employed alone or with other aspects of the system.

Figure 7:
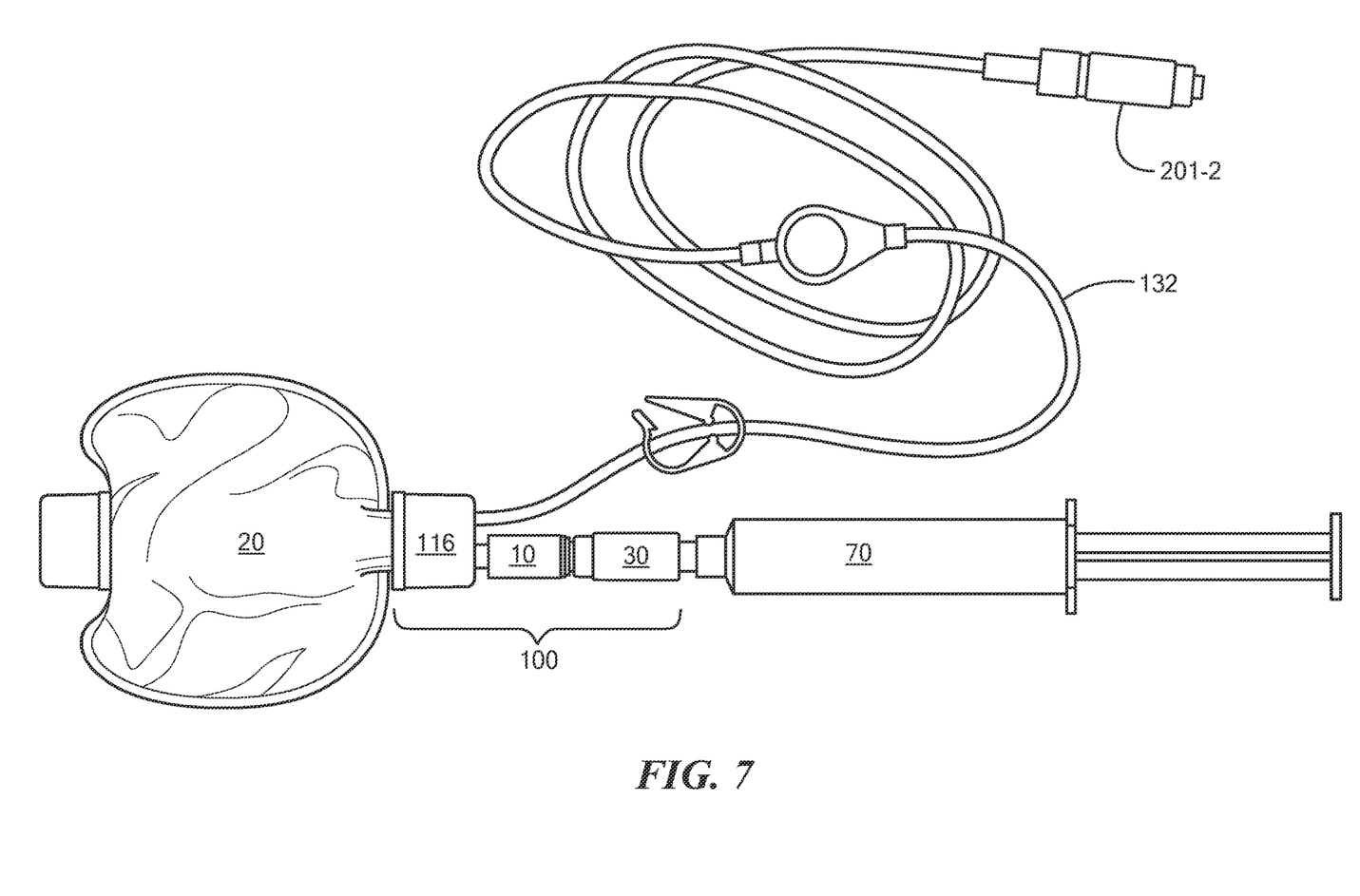
FIG. 7 shows the direct connect system of FIG. 6 engaged for fluidic delivery.

FIG. 7 shows the direct connect system of FIG. 6 engaged for fluidic delivery. The syringe engages the closed male luer 30, including the protrusion 242, which in turn engages an ingress fitting 10 having a check valve. The male luer 30 and ingress fitting 10 define a source side disconnection point 201-1. One-way fluidic travel is enforced by unidirectional valve 116, which regulates inflow and outflow to ensure medication travels only to the patient via supply line 132, and restricts backflow out through the source vessel 32.

While the system and methods defined herein have been particularly shown and described with references to embodiments thereof, it will be understood by those skilled in the art that various changes in form and details may be made therein without departing from the scope of the invention encompassed by the appended claims.

What is claimed is:

1. A medicinal pumping device, comprising:
   an expandable surround around a medicinal repository adapted to store a volume of fluid for intravenous injection based on a pressure in the expandable surround;
   a safety valve defining an ingress port configured to receive the volume of fluid from a fill tube for infusion via a delivery vessel fluidically coupled to the medicinal repository for unidirectional transport of the fluid therefrom;
   the safety valve in fluidic communication between the ingress port and the medicinal repository, the safety valve operable to engage an ingress fitting at an end of and supplied by the fill tube for permitting unidirectional fluidic transfer from the fill tube via the ingress port into the medicinal repository when engaged with the ingress fitting; and
   a closure in the safety valve adapted to seal the ingress port upon disengagement of the ingress fitting for retaining fluid in either the medicinal repository or the fill tube, the closure providing a single point of fluidic disconnect and enforcing unidirectional flow to encapsulate the fluid in the medicinal repository, wherein disengagement of the ingress fitting from the safety valve at the ingress port provides for sealing residual fluid in the fill tube, the closure responsive to the pressure in the expandable surround for enforcing the unidirectional flow.

2. The device of claim 1 wherein the closure is responsive to a protrusion on the ingress fitting for permitting fluid flow, the protrusion responsive to engagement with the safety valve at the ingress port for permitting fluid flow only when engaged.

3. The device of claim 1 wherein the closure includes a resilient surface adapted to deform towards an inflow direction into the medicinal repository in response to a protrusion on the ingress fitting, and adapted to revert to a closed position from at least one of retraction of the protrusion or outflow pressure from the medicinal repository.

4. The device of claim 1 wherein the closure further comprises at least one interference surface configured to dispose into a sealing engagement within the safety valve at the ingress port.

5. The device of claim 4 wherein the at least one interference surface is responsive to permit fluid ingress based on fluidic flow into the medicinal repository and restrict outflow through the ingress port in response to reverse fluidic pressure based on an attachment of the fill tube.

6. The device of claim 4 wherein the at least one interference surface is adapted to dispose to a sealed position responsive to fluidic pressure in an outflow direction from the medicinal repository.

7. The device of claim 6 wherein the at least one interference surface is adapted to dispose to an open position in response to insertion of a protrusion on the ingress fitting.

8. The device of claim 4 wherein the at least one interference surface is hingedly attached to an outer wall of the safety valve at the ingress port for opening inward towards an interior of the medicinal repository in response to insertion of a protrusion on the ingress fitting, the at least one interference surface returning to a closed position upon either reverse fluid flow or protrusion retraction.

9. The device of claim 1 further comprising a delivery port attached to the medicinal repository, the delivery port coupled to the delivery vessel and having a check valve adapted to retain residual fluid upon disconnection from patient delivery.

10. The device of claim 1 wherein the safety valve is adapted to retain a residual fluid volume upon disconnection of the fill tube from the ingress port.

11. The device of claim 1 wherein the ingress fitting has a protrusion responsive to disengagement with the safety valve for isolating a residual fluid volume in the vessel supplying the ingress fitting.

12. A medicinal pumping system, comprising:
    an expandable surround around a medicinal repository adapted to store a volume of fluid for intravenous injection based on a pressure in the expandable surround;
    a safety valve defining an ingress port configured to receive the volume of fluid for storage in the medicinal repository from a fill tube for infusion via a delivery vessel;
    the delivery vessel configured for transporting the volume of fluid in the medicinal repository for infusion, the delivery vessel fluidically coupled to the medicinal repository for unidirectional transport of the fluid therefrom;
    the safety valve in fluidic communication between the ingress port and the medicinal repository, the safety valve operable to engage an ingress fitting at an end of and supplied by the fill tube for permitting unidirectional fluidic transfer from the fill tube via the ingress port into the medicinal repository when engaged with the ingress fitting; and
    a closure in the safety valve adapted to seal the ingress port upon disengagement of the ingress fitting for retaining fluid in either the medicinal repository or the fill tube,
    the safety valve and a patient injection fitting each providing a single point of fluidic disconnect and enforcing unidirectional flow to encapsulate the fluid in the medicinal repository and configured to prevent spillage of a residual volume of fluid, wherein disengagement of the ingress fitting from the safety valve provides for sealing residual fluid in the fill tube, the closure responsive to the pressure in the expandable surround for enforcing the unidirectional flow.

\* \* \* \* \*